United States Patent
Connelly, Jr.

(10) Patent No.: US 6,852,238 B2
(45) Date of Patent: Feb. 8, 2005

(54) LAYERED TABLET WATER TREATMENT COMPOSITIONS AND METHOD OF USE

(75) Inventor: Thomas V. Connelly, Jr., Kirkwood, MO (US)

(73) Assignee: Steller Technology Company, Sauget, IL (US)

( * ) Notice: Subject to any disclaimer, the term of this patent is extended or adjusted under 35 U.S.C. 154(b) by 55 days.

(21) Appl. No.: 10/064,929

(22) Filed: Aug. 29, 2002

(65) Prior Publication Data
US 2004/0040915 A1 Mar. 4, 2004

(51) Int. Cl.⁷ .............................. C02F 1/76; C01B 7/00
(52) U.S. Cl. ..................... 210/753; 252/175; 252/187.1
(58) Field of Search ......................... 210/749, 753–756, 210/764, 169, 198.1; 422/37; 252/175, 187.1; 510/224, 225; 424/464, 472, 661, 665

(56) References Cited

U.S. PATENT DOCUMENTS

| | | | |
|---|---|---|---|
| 3,873,685 A * | 3/1975 | Kibbe et al. ............... 424/405 |
| 4,828,745 A | 5/1989 | Jeschke et al. |
| 4,846,979 A | 7/1989 | Hamilton |
| 5,133,892 A * | 7/1992 | Chun et al. ................. 510/224 |
| 5,240,713 A | 8/1993 | Ayer |
| 5,283,065 A | 2/1994 | Doyon et al. |
| 5,407,598 A * | 4/1995 | Olson et al. ........... 252/186.35 |
| 5,549,913 A | 8/1996 | Colombo et al. |
| 5,700,377 A * | 12/1997 | Cox ........................... 210/724 |
| 5,738,874 A | 4/1998 | Conte et al. |
| 5,783,540 A | 7/1998 | Secemski et al. |
| 5,783,550 A | 7/1998 | Kuriyama et al. |
| 5,837,663 A | 11/1998 | Nicholson et al. |
| 5,962,387 A | 10/1999 | Gorlin et al. |
| 6,083,533 A | 7/2000 | Cremer |
| 6,136,344 A | 10/2000 | Depui et al. |
| 6,149,821 A * | 11/2000 | Rounds et al. ............... 210/751 |
| 6,149,940 A | 11/2000 | Maggi et al. |
| 6,183,778 B1 | 2/2001 | Conte et al. |
| 6,183,845 B1 | 2/2001 | Ikemoto |
| 6,194,368 B1 | 2/2001 | Waschenbach et al. |
| 6,589,925 B1 * | 7/2003 | Binstock et al. ............. 510/224 |

FOREIGN PATENT DOCUMENTS

JP   57095804 A * 6/1982

* cited by examiner

Primary Examiner—Frank M. Lawrence
(74) Attorney, Agent, or Firm—Blackwell Sanders Peper Martin LLP

(57) ABSTRACT

The present invention relates generally to novel water treatment compositions. More particularly, the invention relates to solid water treatment compositions in the form of a water soluble tablet containing at least one halogen source and at least a pH compensating source in a layered tablet wherein one layer comprises the halogen source and another layer comprises a pH compensating source. Methods for controlling water biofouling and disinfecting water systems, particularly swimming pools and spas, are disclosed.

28 Claims, 1 Drawing Sheet

LAYERED TABLET WATER TREATMENT COMPOSITIONS AND METHOD OF USE

BACKGROUND OF INVENTION

The provision of safe and clean water that is also visually attractive to the user is important in municipal, industrial, and recreational applications. Conventional water treatments employ physical, chemical, and biological processes either alone or in combination to produce water of acceptable quality.

In applications where water is intended for human contact or consumption, the water must be treated so that it is aesthetically pleasing in terms of taste, color, turbidity, odor, and pH, environmentally safe, and effectively free of pathogens and chemicals responsible for both acute and chronic illness. Conventional methods use chemicals as oxidizers, biocides, algaecides, and pH buffers for the treatment of water. Typically, the chemicals are added to the water separately as part of an overall water maintenance or purification program. The water is monitored on an hourly, daily, or weekly basis, and when a particular treatment parameter is not acceptable or in compliance with regulatory levels, the appropriate amount of the necessary chemical is added. Often, treatment of one water quality parameter causes another water quality parameter to change. Conventional treatment, therefore, employs a continuous balancing process of monitoring water quality parameters and dosing with various chemicals to create and to maintain the appropriate water quality.

It must be appreciated that potable water typically has a pH of 8.3 with a total alkalinity of 50 ppm and a calcium content of 100 ppm. The term "total alkalinity" is used to describe the total amount of dissolved alkaline substances in water, excluding calcium. "Dissolved solids" in suspension in swimming pool water, predominantly provided by the total alkalinity and calcium in the water, give the water its "blue" color when sunlight reflects off the water. Thus, reductions in the amount of dissolved solids in water will result in the water having an increasingly green color. It will be appreciated that it is desirable to provide a water purification composition that provides sufficient dissolved solids to give the water a blue color.

In applications such as swimming pools and spas, chemical combinations attempt to provide a complete water quality treatment. For example, U.S. Pat. No. 5,700,377, issued to Cox on Dec. 23, 1997, discloses a complete treatment for the purification of water in non-porous swimming pools, obviating the need for the addition of any other compounds to the water. The chemical composition of Cox includes a peroxide compound, an ammonium-based biocidal compound, an acidic compound, a basic compound, a calcium-releasing basic compound, and EDTA in the form of a "kit" or mixture. The composition is added to the water when the pH of that water is outside the human comfort zone of 7.2 to 7.6 in order to bring the pH within the zone range. Therefore, water clarification is combined with a pH adjustment. However, the use of such mixtures exposes the user to the disadvantage of maintaining the mixture in a condition that prohibits the reaction of the basic material with the acidic materials. Also, such reaction occurs upon addition of the mixture to the water being treated.

Attempts to combine various chemicals into a convenient tablet form have been known. Tabletting of various chemicals for release at various times has been used extensively in the administration of medicine. Typical examples of such tablets are found in U.S. Pat. No. 6,183,778 issued to Conte et al. on Feb. 6, 2001; U.S. Pat. No. 6,149,940 issued to Maggi et al. on Nov. 21, 2000; U.S. Pat. No. 6,136,344 issued to Depui et al. on Oct. 24, 2000; and U.S. Pat. No. 6,083,533 issued to Cremer on Jul. 4, 2000. It can be appreciated that time release of medicaments has great value in treatment regimens and tablets that provide such properties are numerous. The above list is a mere sample of those references wherein tablets contain various layers having different solubility rates in digestive fluids.

Another industry finding great utility with multi-layered tablets having various components for differing purposes is the automatic dishwashing detergent industry. There, the advantage of various wash cycles of automatic dishwashers provide an opportunity to build a multi-layer tablet wherein several agents are combined in a layered fashion to supply the appropriate cleaning chemical at the propitious time in the wash cycle. A typical example of such disclosures are U.S. Pat. No. 6,194,368, issued to Waschenbach et al. on Feb. 27, 2001, wherein the first layer of a dishwashing detergent tablet contains an activated, halogen-free bleach, and silver/copper corrosion inhibitor in an outer layer and a bleach activator in another layer. U.S. Pat. No. 5,962,387, issued to Gorlin et al. on Oct. 5, 1999, discloses a three-layer tablet wherein each layer contains a different detergent formulation. As the wash cycle proceeds, a different formulation believed optimum for each portion of the cycle is exposed. In U.S. Pat. No. 5,837,663, issued to Nicholson et al. on Nov. 17, 1998, there is disclosed a two-layer tablet for automatic dish washing where a first layer contains a buffer, a builder and an enzyme which dissolves at a pH of 9–11. A second layer is provided containing a per acid and a acidity agent having a melting point of from 35 to 50 degrees C. along with a carrier. The second layer delivers a pH of from 6.5–9. The release order is said to allow optimum removal of stains and food from the dishes. Another example of a multi-layer tablet for use in automatic dishwashers allowing for different pH levels during a single wash cycle appears in U.S. Pat. No. 5,783,540, issued to Secemski et al. on Jul. 21, 1998. In this patent, an oxygen bleach, a buffer system to deliver a pH of 8.5–11, a builder and an enzyme are contained in one layer while a second layer is provided containing an acidity agent to provide a pH below 9, a carrier having a high melting point for the acidity agent and an anti-scaling agent. In theory, the high melting carrier is dispersed in the high temperature final rinse cycle thereby providing a superior finish to the articles, especially glass. Other examples of multi-layer tablets used in automatic dish washing machines are found in U.S. Pat. No. 5,549,913 issued to Colombo et al. on Aug. 27, 1996; U.S. Pat. No. 5,133,892 issued to Chun et al. on Jul. 28, 1992; and U.S. Pat. No. 4,828,745 issued to Jeschke et al. on May 9, 1989.

The use of tablets for administering halogen-containing chemicals to swimming pools has long been known. Usually the tablets are placed in the pool water system at points where flowing water is provided such as in the filtration system skimmer or in a floating basket at the surface of the pool. As noted above, in most instances, the condition of the pool water is monitored periodically to insure a desirable pH level is maintained while administering a generally acid contributing halogen containing compound. A two-layer tablet for chlorination of water systems is disclosed in U.S. Pat. No. 3,873,685 issued to Kibbel, Jr. et al. on Mar. 25, 1975. This patent discloses the combination of contiguous layers in one tablet wherein one layer contains a fast dissolving halogen-releasing agent while a second layer provides a slower dissolving halogen-releasing agent. A relatively fast dissolving halogen-releasing agent, sodium dichloroisocyanurate dihydrate is contained in one discrete layer and trichloroisocyanuric acid is contained in another layer. Various geometric shapes of tablets are suggested wherein the discrete portions of the ingredients are provided in structures having either a layered structure or an inner core and outer core such as in the shape of a rod or oval ball. While providing a measure of convenience in placing halogen-releasing materials in the water, the need still arises to monitor and control the total alkalinity of the water as well as the pH level, particularly in swimming pools.

Because of the proximity of reactive chemicals such as an acidic material and a basic material to each other is a single composition, the production of such products have proven to have limited or no commercial value because of the danger presented by the possibility of an exothermic reaction occurring during storage and shipping of large quantities of such materials.

SUMMARY OF INVENTION

The present invention relates generally to water treatment compositions and methods of use. More particularly, the invention relates to solid water treatment compositions comprising a halogen source and a pH compensating source and methods of using such compositions.

A safe and effective combination of a halogen source with a pH compensating source has now been discovered in the creation of a multi-layered tablet. The water treatment composition of this invention comprises a multi-layer tablet wherein one discrete layer contains at least one halogen source and a second discrete layer contains at least a pH compensating source. Materials useful in this invention are solid, particulate materials capable of being compressed into separate, contiguous layers providing a structurally strong, storage-stable tablet. The ratio of the amount of halogen source to the amount of pH compensating source is adjusted to provide, when dissolved in a water system, a pH of from 7.2–7.8 and total alkalinity of from 80 to 150 ppm, depending upon the materials of construction of the pool, spa or other form of containment of the water to be treated. Such amounts can be calculated as will be demonstrated below. The multi-layered tablets are conveniently prepared by known methods of tablet formation.

There is also provided in accordance with this invention, a method of administering a biocidal amount of a halogen source to a water system while simultaneously adjusting the pH and total alkalinity of the water by means of adding to the water a tablet of this invention containing both a halogen source and an alkaline source in discrete, contiguous layers in a single tablet that dissolves in the water system. It has been discovered that the layered tablet configuration provides separated surfaces of a stable tablet from which each layer is able to dissolve in the water at a rate of dissolution substantially independent of the other layer. Minimal direct reaction occurs between the materials in the separate layers as they separately dissolve providing the needed biocidal action while also providing compensating alkalinity.

The solid water treatment tablets of this invention may also comprise excipients and other inert or active additives.

DETAILED DESCRIPTION

Figure 1:
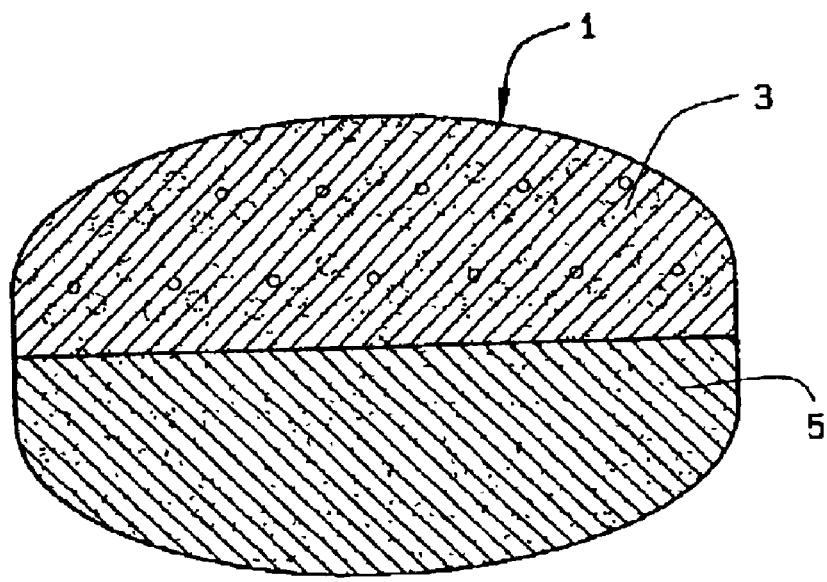
FIG. 1 shows a typical two-layer tablet of this invention, wherein tablet 1 provides a halogen source layer 3 and a pH compensating source layer 5. As noted above, the two separate layers embodied in a structurally stable tablet maintains the two layers separate and apart during dissolution in the aqueous medium. Such separation is a large factor in the element of safety, not only during actual use but also during shipping and storage of the tablet.

The water treatment composition of this invention comprises a tablet containing at least two contiguous layers, one layer comprising at least one halogen source and a second layer comprising at least one pH-compensating source. It has been discovered that, with usual precautions to prevent contamination with water and water bearing substances, the tablets of this invention are stable. Surprisingly, each layer of the inventive tablet dissolves at a rate that is dependent upon the properties of each layer separate and apart from the other layer.

As employed in this invention, the term "water system" means a defined quantity of water contained in a vessel such as a swimming pool, industrial cooling system, pond, fountain, etc.

As employed in this invention, the term "inert" means a material that is non-reactive with a halogen source of a pH compensating source.

As used herein, the "at least one halogen source" comprises one or more compounds that provide hypohalous acid, HOX or hypohalite ion, or OX species wherein X is halogen when dissolved in water.

As used herein, the term "alkaline source" refers to compounds containing metal cations within group IA and IIA referenced in the periodic table. In particular, this includes cations of the alkali metals lithium, sodium, potassium, rubidium, and cesium; and further includes cations of the alkaline earth metals beryllium, magnesium, calcium, strontium, and barium in compounds providing, in aqueous solution, a pH above 7. Typical compounds usable as an alkaline source in this invention include: alkaline hydroxides; alkaline carbonates; alkaline bicarbonates; alkaline phosphates; alkaline silicates; and alkaline borates. Particularly preferred alkaline sources are sodium carbonate and sodium bicarbonate.

As employed herein, the term "basic in aqueous solution" means a material that, alone in aqueous solution, provides a pH above 7.

As employed herein, the term "acid in aqueous solution" means a material that, alone in aqueous solution provides a pH below 7.

Typical halogen sources may comprise any halogen-containing compound that provides a halogen ion in aqueous solution. Halogen ions such as chlorine, bromine, and iodine may be particularly useful. Preferably, the halogen source comprises chlorine or bromine or a combination thereof. Representative halogen sources, for example, include trichloroisocyanuric acid (TCCA), dichloroisocyanuric acid (DCCA), monochloroisocyanuric acid, potassium dichloroisocyanuric acid, sodium dichloroisocyanuric acid dihyrate, anhydrous sodium dichloroisocyanuric acid, tribromoisocyanuric acid, dibromoisocyanuric acid, monobromoisocyanuric acid, monobromodichloroisocyanuric acid, dibromomonochloroisocyanuric acid, calcium hypochlorite, lithium hypochlorite, 1,3-dichloro-5,5-dimethylhydantoin (DCDMH), 1,3-dibromo 5,5-dimethylhydantoin, 1-bromo-3-chloro-5,5-dimethylhydantoin (BCDMH), 1-bromo-3- chloro-5-methyl-5-ethylhydantoin (BCEMH), 1,3-dichloro-5-methyl-5-ethylhydantoin, 1,3-dichloro-5,5-dimethylhydantoin, 1,3-dibromo-5,5-dimethyhydantoin, trichloromelamine, tribromomelamine and mixtures thereof. The halogen source may further comprise one mole of trichloroisocyanuric and four moles of potassium dichloroisocyanuric acid; compositions comprising trichloroisocyanuric acid and potassium bromide; and compositions comprising about 60% by weight 1-bromo-3-chlorodimethylhydantoin, about 30% by weight 1,3-dichloro-5,5-dimethylhydantoin and about 10% by weight 1,3-dichloro-5-ethyl-5-methylhydantoin.

Halogen sources are readily available in commercial form. The most preferred halogen source is TCCA and DCCA. Other preferred halogen sources are BCDMH, DCDMH and BCEMH.

Solid forms of the halogen source and water treatment composition can be blended powders, compressed granules, briquettes, pellets, extrusions, agglomerations, flakes, sheets, cast blocks, compressed blocks and the like.

The pH-compensating source employed in the layered tablet of this invention is any solid, compactable material soluble in aqueous media to provide a pH-compensating source in the water. Of course, where water is intended for human contact or consumption, the pH-compensating source must be non-toxic at concentrations adequate to provide the pH and total alkalinity totals noted above.

Typical alkaline sources include alkali metal or alkaline earth carbonates, alkaline or alkaline earth bicarbonate, an alkaline phosphate, an alkaline silicate, an alkaline borate, and mixtures of these compounds. More particularly, preferred alkaline sources useful in this invention include sodium carbonate, potassium carbonate, lithium carbonate, sodium bicarbonate, potassium bicarbonate and lithium bicarbonate. Typical acidic pH materials (where the halogen source contributes basic pH to the water) include sodium bisulfate or a combination of soot ash and sodium bicarbonate.

In the water treatment method of this invention the one or more layered tablets as described above are inserted into the water body to be treated whereby the layers of the tablet simultaneously dissolve at independent rates. Generally the alkaline source layer will dissolve at a faster rate than the halogen source layer.

Proper water balance for pools and spas means maintaining pH, total alkalinity, calcium hardness and temperature in ranges that will make the water neutral so as to avoid a tendency to either corrode or to scale. The proper range for these parameters is generally as follows:

TABLE 1

| | |
|---|---|
| pH | 7.2–7.6 |
| Total Alkalinity | 80–120 ppm for plaster pools 100–150 ppm for Vinyl and Painted pools |
| Calcium Hardness | 90–275 |
| Temperature | 76–84° F. for Pools 95–104° F. for Spas |

Calcium hardness for a tablet can range from about 90 to about 275 with a preferred range of about 141 to about 200 and a most preferred range from about 200 to about 275 and higher. The density for a tablet can range from about 1.3 grams per cubic centimeter (81.15 pounds per cubic foot) to about 1.5 grams per cubic centimeter (93.63 pounds per cubic foot) with a preferred range from about 1.51 grams per cubic centimeter (94.26 pounds per cubic foot) to about 1.7 grams per cubic centimeter (106.12 pounds per cubic foot) with a most preferred range of 1.71 grams per cubic centimeter (106.74 pounds per cubic foot) to about 2.1 grams per cubic centimeter (131.09 pounds per cubic foot).

Various chlorine sources and pH compensating sources are employed in the layered tablet and process of this invention. Typical materials and the effect such material have in a body of water being treated are listed below in Table 2 wherein the following abbreviations are employed:
TCCA:trichloroisocyanuric acid
SDCCA: sodium dichloroisocyanuric acid
Hypo:Hypochlorite
BCDMH:1-bromo-3-chloro-5,5-dimethylhydantoin
BCEMH:1-bromo-3-chloro-5-methyl-5-ethylhydantoin
DBDMH:1,3-dibromo-5,5-dimethylhydantoin

TABLE 2

| Halogen Compound | TCCA | SDCCA | CalHypo | Lithium Hypo | BCDMH | BCEMH | DBDMH |
|---|---|---|---|---|---|---|---|
| Chemical State | Solid | Solid | Solid | Solid | Solid | Solid | Solid |
| Typical Effect | Lowers pH 2.9 | Negligible pH 6.0 | Raises pH 11.7 | Raises pH 10.5 | Lowers pH x | Lowers pH 3.6 | Lowers pH x |
| Relative Solubility | Slow | Very Fast | Fast | Very Fast | Slow | Slow | Slow |
| To Re-Adjust pH | Add Base | +Minor Base | Add Acid | Add Acid | Add Base | Add Base | Add Base |

From the above it can be seen that the layered tablet of this invention may contain either a base or an acid depending upon the effect on pH of the halogen source. All of the solid forms above can be tabletted in order to prolong the life of the product. As a practical matter, the solid halogen compounds that dissolve "very fast" are employed differently than those having a slower dissolution rate. For example, SDCCA would only last minutes while the powdered or granular form would last only a few seconds in the solid state when placed in water. A tablet of SDCCA would have utility as a "unit dose" for quick action rather than for any extended treatment period as would other layered tablets of this invention.

The halogen sources of this invention may be mixed and mixtures of these compounds compacted or formed into a layer tablet of this invention. Accordingly, mixtures of any of the halogen sources noted above, TCCA, BCDMH, BCEMH, DBDMH may be combined in measured ratios and compacted into one of the layers of the layered tablet of this invention. The calculated increase or decrease of pH contributed by the halogen source is off-set with an appropriate amount of acid or base material in the other layer in order to maintain the proper water pH balance thereby providing water that does not corrode or scale.

Figure 2:
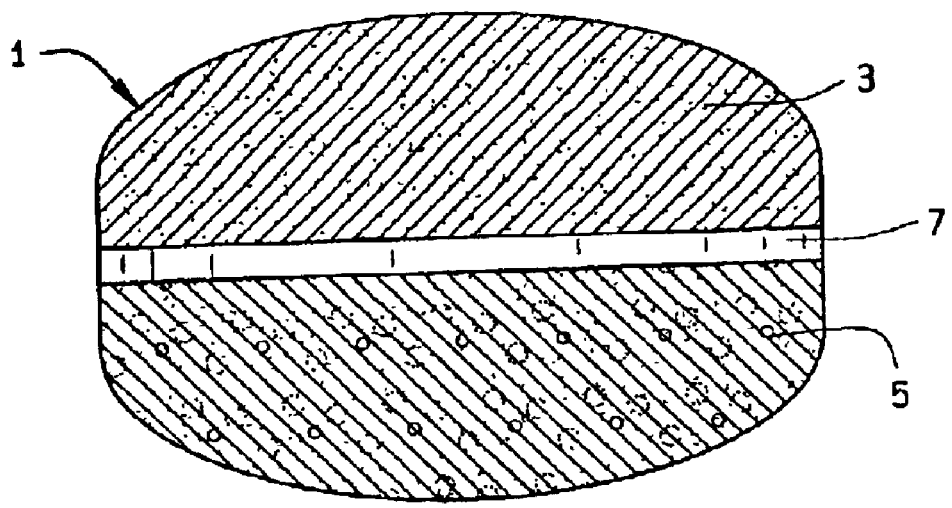
FIG. 2 shows a typical three-layer tablet of this invention, wherein an inert boundary layer 7 is included in the tablet to physically separate the layer containing the halogen source 3 from the layer containing the pH-compensating source 5.

As shown in FIGS. 1 and 2, the acids and bases must be added separately since intimate mixtures of either acids or bases with a given halogen compound will destroy the integrity of the tablet and the advantage of slow solubility. A boundary layer may be employed when a particular combination of halogen source and pH compensating source is desirably maintained apart during manufacture, shipping, storage and use. Any suitable boundary material may be employed and is generally one that is non-reactive to either the halogen source or the pH compensating source and also is neutral in water solution (no effect on pH). As is usual in water treatment materials, the inert boundary layer also is not harmful to humans or construction material holding the treated water. Examples of suitable boundary (barrier) materials include members of the alkali metal salts family such as sodium chloride, sodium sulfate, sodium tripolyphosphate or sodium bicarbonate.

The ratio of halogen source to pH compensating source may vary widely. Because water quality varies widely the ratio of halogen source to pH compensating source can be tailored to the water quality in various areas of the country. For example, the amount of pH compensating source may vary from about 5% by weight to about 50% by weight of the halogen source. Adjusting the ratio of each component of the layered tablet of this invention will enable the operator of the water system to balance the water with respect to total alkalinity and pH while maintaining proper halogen content to prevent deterioration of water quality due to impurities.

Presses that can be utilized to create the tablets include, but are not limited to: Baldwin, (Press Models 20, 75A, 45, 45A, 200 and 200A), which are no longer being manufactured but can be purchased from previously-owned equipment vendors: Stokes, (Press Models R, R4, 294, 280g, s5, 210 and Summit™), manufactured by Elizabeth Carbide Die Company Incorporated, having a place of business at 601 Linden Street, McKeesport, Pa. 15132; Korsch America, Inc., (Press Models TRP 900, EK4 and EK5), having a place of business at 18 Bristol Drive, South Easton, Mass. 02375; Courtoy N.V., (Press Models R5 and 46), having a place of business at Bergensesteenweg 186, 1500 Halle, Belgium; Vector, (Press Model Gladiator), having a place of business at 675 44$^{th}$ Street, Marion, Iowa 52302; Dorst America Incorporated, having a place of business at 64 S. Commerce Way, Bethlehem, Pa. 18017; Hydramet America Incorporated, having a place of business at 4605 Delemere Blvd., Royal Oak, Mich. 48073; Kux Manufacturing, having a place of business at 12675 Burt Road, Detroit, Mich. 48223; and Pasadena Hydraulics Incorporated, (Press Model PHI B-23), having a place of business at 14955 Salt Lake Avenue, City of Industry, Calif. 91746.

The amount of pressure applied to each individual tablet can range from about 9.07 metric tons (10 short tons) to about 181.44 metric tons (200 short tons) per tablet with a preferred range of pressure from about 31.75 metric tons (35 short tons) to about 45.36 metric tons (50 short tons) and a most preferred amount of pressure being 36.29 metric tons (40 short tons).

EXAMPLE

Layered tablets of this invention were prepared by supplying a halogen source to the cavity of a stainless steel dye of a Korsch Model TRP 900 Laboratory Hand Press. Then, a pH-compensating source was supplied uniformly on top of the halogen source in the same dye cavity. A tabletting force of 200,000 Newtons (44,961.79 pounds) was applied to the layered materials by means of a mating stainless steel plunger. The hardness is over 200.

What is claimed is:

1. A solid, multi-layer water treatment tablet comprising one discrete layer containing at least one halogen source and a second discrete layer containing at least one pH compensating source, wherein the halogen source is acid in an aqueous solution and the pH compensating source is basic in aqueous solution, wherein the halogen source is selected from the group consisting of, anhydrous sodium dichloroisocyanuric acid, tribromoisocyanuric acid, dibromoisocyanuric acid, monobromoisocyanuric acid, monobromodichloroisocyanuric acid, dibromomonochloroisocyanuric acid, 1,3dichloro-5,5-dimethylhydantoin, 1,3-dibromo 5,5-dimethylhydantoin, 1-bromo-3-chloro-5,5-dimethylhydantoin, 1,3-dichloro-5-methyl-5-ethylhydantoin, 1,3-dichloro-5,5-dimethylhydantoin, 1,3-dibromo-5,5-dimethylhydantoin, trichloromelamine, tribromomelamine and mixtures thereof.

2. A solid, multi-layer water treatment tablet comprising one discrete layer containing at least one halogen source and second discrete layer containing at least one pH compensating source, wherein the halogen source is basic in an aqueous solution and the pH compensating source is acid in an aqueous solution, wherein the halogen source is selected from the group consisting of calcium hypochlorite and lithium hypochlorite and wherein the pH compensating source includes an alkali metal bisulfate.

3. The tablet of claim 2, wherein the alkali metal bisulfate includes sodium bisulfate.

4. A solid, multi-layer water treatment tablet comprising one discrete layer containing at least one halogen source and a second discrete layer containing at least one pH compensating source, wherein the halogen source includes trichloroisocyanuric acid and the pH compensating source includes sodium hypochlorite.

5. A solid, multi-layer water treatment tablet comprising one discrete layer containing at least one halogen source and a second discrete layer containing at least one pH compensating source, wherein the halogen source includes one mole of trichloroisocyanuric and four moles of potassium dichloroisocyanuric acid.

6. A solid, multi-layer water treatment tablet comprising one discrete layer containing at least one halogen source and second discrete layer containing at least one pH compensating source, wherein the halogen source comprises about 60% by weight 1-bromo-3-chloro-dimethylhydantoin, about 30% by weight 1,3 dichloro 5,5-dimethylhydantoin and about 10% by weight 1,3-dichloro-5-ethyl-5-methylhydantoin.

7. A solid, multi-layer water treatment tablet comprising, sequentially, one discrete layer comprising at least one halogen source and a second discrete layer comprising an inert boundary layer and a third layer comprising at least one pH compensating source, wherein the boundary layer comprises a material selected from the group consisting of alkali metal chlorides and alkali metal sulfates.

8. A solid, multi-layer water treatment tablet comprising, sequentially, one discrete layer comprising at least one halogen source and a second discrete layer comprising an inert boundary layer and a third layer comprising at least one pH compensating source, wherein the boundary layer comprises an alkali metal chloride.

9. The tablet of claim 8, wherein the alkali metal chloride includes sodium chloride.

10. The tablet of claim 7, wherein the alkali metal sulfate includes sodium sulfate.

11. A solid, multi-layer water treatment tablet comprising, sequentially, one discrete layer comprising at least one halogen source and a second discrete layer comprising an inert boundary layer and a third layer comprising at least one pH compensating source, wherein halogen source is basic in aqueous solution and the pH compensating source is acidic in aqueous solution.

12. A solid, multi-layer water treatment tablet comprising, sequentially, one discrete layer comprising at least one halogen source and a second discrete layer comprising an inert boundary layer and a third layer comprising at least one pH compensating source, wherein the halogen source is acidic in aqueous solution and the pH compensating source is basic in aqueous solution, wherein the halogen source is selected from the group consisting of trichloroisocyanuric acid, anhydrous sodium dichloroisocyanuric acid, tribromoisocyanuric acid, dibromoisocyanuric acid, monobromoisocyanuric acid, monobromodichloroisocyanuric acid, dibromo-monochloroisocyanuric acid, 1,3-dichloro-5,5-dimethylhydantoin, 1,3dibromo 5,5-dimethylhydantoin, 1-bromo-3-chloro-5,5-dimethylhydantoin, 1,3-dichloro-5-methyl-5-ethylhydantoin, 1,3-dichloro-5,5-dimethylhydantoin, 1,3-dibromo-5,5-dimethylhydantoin, trichloromelamine, tribromomelamine and mixtures thereof.

13. A solid, multi-layer water treatment tablet comprising, sequentially, one discrete layer comprising at least one halogen source and a second discrete layer comprising an inert boundary layer and a third layer comprising at least one pH compensating source, wherein the halogen source is basic in aqueous solution and the pH compensating source is acidic in aqueous solution, and wherein the halogen source is selected from the group selected from the group consisting of calcium hypochlorite and lithium hypochlorite.

14. A solid, multi-layer water treatment tablet comprising, sequentially, one discrete layer comprising at least one halogen source and a second discrete layer comprising an inert boundary layer and a third layer comprising at least one pH compensating source, wherein the halogen source is acidic in aqueous solution and the pH compensating source is basic in aqueous solution, and wherein the pH compensating source includes sodium bicarbonate.

15. A solid, multi-layer water treatment tablet comprising, sequentially, one discrete layer comprising at least one halogen source and a second discrete layer comprising an inert boundary layer and a third layer comprising at least one pH compensating source, wherein the halogen source is basic in aqueous solution and the pH compensating source is acidic in aqueous solution, wherein the halogen source is selected from the group selected from the group consisting of calcium hypochlorite and lithium hypochlorite, and wherein the pH compensating source includes an alkali metal bisulfate.

16. The tablet of claim 15, wherein the alkali metal bisulfate includes sodium bisulfate.

17. A solid, multi-layer water treatment tablet comprising, sequentially, one discrete layer comprising at least one halogen source and a second discrete layer comprising an inert boundary layer and a third layer comprising at least one pH compensating source, wherein the halogen source includes trichloroisocyanuric acid and the pH compensating source includes sodium hypochlorite.

18. A solid, multi-layer water treatment tablet comprising, sequentially, one discrete layer comprising at least one halogen source and a second discrete layer comprising an inert boundary layer and a third layer comprising at least one pH compensating source, wherein the halogen source comprises one mole of trichloroisocyanuric and four moles of potassium dichloroisocyanuric acid.

19. A solid, multi-layer water treatment tablet comprising, sequentially, one discrete layer comprising at least one halogen source and a second discrete layer comprising an inert boundary layer and a third layer comprising at least one pH compensating source, wherein the halogen source comprises about 60% by weight 1-bromo-3-chloro-dimethylhydantoin, about 30% by weight 1,3-dichloro-5,5-dimethylhydantoin and about 10% by weight 1,3-dichloro-5-ethyl-5-methylhydantoin.

20. A method of treating a water system, which comprises adding to the water a solid, multi-layer water treatment tablet comprising one discrete layer containing at least one halogen source and a second discrete layer containing at least one pH compensating source, wherein the halogen source is acidic in an aqueous solution and the pH compensating source is basic in an aqueous solution, wherein the halogen source is selected from the group consisting of anhydrous sodium dichloroisocyanuric acid, tribromoisocyanuric acid, dibromoisocyanuric acid, monobromoisocyanuric acid, monobromodichloroisocyanuric acid, dibromomonochloroisocyanuric acid, 1,3-dichloro-5,5-dimethylhydantoin, 1,3-dibromo 5,5-dimethylhydantoin, 1-bromo-3-chloro-5,5-dimethylhydantoin, 1,3-dichloro-5-methyl-5-ethylhydantoin, 1,3-dichloro-5,5-dimethylhydantoin, 1,3-dibromo-5,5-dimethylhydantoin, trichloromelamine, tribromomelamine and mixtures thereof.

21. A method of treating a water system, which comprises adding to the water a solid, multi-layer water treatment tablet comprising one discrete layer containing at least one halogen source and a second discrete layer containing at least one pH compensating source, wherein the halogen source is basic in an aqueous solution and the pH compensating source is acidic in an aqueous solution, wherein the halogen source is selected from the group consisting of calcium hypochlorite and lithium hypochlorite and wherein the pH compensating source includes an alkali metal bisulfate.

22. A method of treating a water system of claim 21, wherein the alkali metal bisulfate includes sodium bisulfate.

23. A method of treating a water system, which comprises adding to the water a solid, multi-layer water treatment tablet comprising one discrete layer containing at least one halogen source and a second discrete layer containing at least one pH compensating source, wherein the halogen source includes trichloroisocyanuric acid and the pH compensating source includes sodium hypochlorite.

24. A method of treating a water system, which comprises adding to the water a solid, multi-layer water treatment tablet comprising one discrete layer containing at least one halogen source and a second discrete layer containing at least one pH compensating source, wherein the halogen source comprises one mole of trichloroisocyanuric and four moles of potassium dichloroisocyanuric acid.

25. A method of treating a water system, which comprises adding to the water a solid, multi-layer water treatment tablet comprising one discrete layer containing at least one halogen source and a second discrete layer containing at least one pH compensating source, wherein the halogen source comprises about 60% by weight 1-bromo-3-chlorodimethylhydantoin, about 30% by weight 1,3 dichloro 5,5 dimethylhydantoin and about 10% by weight 1,3-dichloro-5-ethyl-5-methylhydantoin.

26. A solid, multi-layer water treatment tablet comprising one discrete layer containing at least one halogen source and a second discrete layer containing at east one pH compensating source, wherein the halogen source includes one mole of trichloroisocyanuric and four moles of anhydrous sodium dichloroisocyanuric acid.

27. A solid, multi-layer water treatment tablet comprising, sequentially, one discrete layer comprising at least one halogen source and a second discrete layer comprising an inert boundary layer and a third layer comprising at least one pH compensating source, wherein the halogen source comprises one mole of trichloroisocyanuric and four moles anhydrous sodium dichloroisocyanuric acid.

28. A method of treating a water system, which comprises adding to the water a solid, multi-layer water treatment tablet comprising one discrete layer containing at least one halogen source and a second discrete layer containing at least one pH compensating source, wherein the halogen source comprises one mole of trichloroisocyanuric and four moles of anhydrous sodium dichloroisocyanuric acid.

* * * * *